United States Patent [19]

Goto

[11] Patent Number: 4,853,152
[45] Date of Patent: Aug. 1, 1989

[54] CYCLOHEXANE DERIVATIVE

[75] Inventor: Yasuyuki Goto, Ichihara, Japan

[73] Assignee: Chisso Corporation, Japan

[21] Appl. No.: 268,184

[22] Filed: Nov. 7, 1988

[30] Foreign Application Priority Data

Nov. 16, 1987 [JP] Japan ............................. 62-289132

[51] Int. Cl.$^4$ .................. G02F 1/13; C09K 19/30; C07C 25/18; C07C 121/60
[52] U.S. Cl. .................... 252/299.63; 350/350 R; 558/425
[58] Field of Search ............... 252/299.63; 350/350 R; 558/425

[56] References Cited

U.S. PATENT DOCUMENTS

| | | | |
|---|---|---|---|
| 4,514,044 | 4/1985 | Gunjima et al. | 252/299.63 |
| 4,551,264 | 11/1985 | Eidenschink et al. | 252/299.63 |
| 4,606,845 | 8/1986 | Romer et al. | 252/299.63 |
| 4,621,901 | 11/1986 | Petrzilka et al. | 252/299.63 |
| 4,630,896 | 12/1986 | Petrzilka et al. | 252/299.63 |
| 4,659,502 | 4/1987 | Fearon et al. | 252/299.63 |
| 4,710,315 | 12/1987 | Schad et al. | 252/299.63 |
| 4,724,097 | 2/1988 | Romer et al. | 252/299.63 |

FOREIGN PATENT DOCUMENTS

| | | | |
|---|---|---|---|
| 205998 | 12/1986 | European Pat. Off. | 252/299.63 |
| 280902 | 9/1988 | European Pat. Off. | 252/299.63 |
| 61-501920 | 9/1986 | Japan | 252/299.63 |
| 62-103057 | 5/1987 | Japan | 252/299.63 |

Primary Examiner—Teddy S. Gron
Attorney, Agent, or Firm—Leydig, Voit & Mayer

[57] ABSTRACT

A compound having a relatively low viscosity, a broad nematic phase temperature range, a good compatibility with other liquid crystal components at low temperatures and a positive large dielectric anisotropy value, and a liquid crystal composition having a low viscosity and capable of realizing a low driving threshold voltage of display elements are provided, which compound is a cyclohexane derivative expressed by the formula

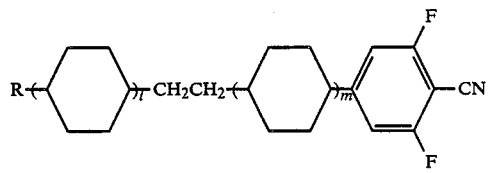

wherein R is 1–10C alkyl group, l is 1 or 2, m is 0 or 1 and l+m=2.

4 Claims, No Drawings

CYCLOHEXANE DERIVATIVE

BACKGROUND OF THE INVENTION

This invention relates to a cyclohexane derivative used as a component of liquid crystal materials and a composition containing the same.

Display devices which liquid crystals are applied thereto utilize an electro-optic effect based on the anisotropies of the dielectric constant and the electric conductivity of liquid crystal substances. Liquid crystal display modes include various ones such as dynamic scattering mode, twist nematic mode, phase transition mode, DAP mode, guest-host mode, etc. Properties required for liquid crystal substances used for liquid crystal display vary depending on the respective liquid crystal display modes, and a broad mesomorphic range, stabilities to moisture, air, light, heat, electricity, etc., and others and commonly required for any display modes. Further, it is also desired that when liquid crystal substances are used for liquid crystal display devices, the resulting display elements have a short response time and can be driven under a voltage as low as possible. At present, however, there is no single compound which satisfies all of these requirements, but practically, liquid crystalline mixtures obtained by mixing compound(s) similar to liquid crystal compounds with several kinds of liquid crystal compounds have been used.

Recently, as the use applications of liquid crystal displays have been enlarged, specific features required for liquid crystal materials have also become severer. For example, as seen in the case of on-vehicle displays where the service temperature range is in the range of $-40°$ to $+100°$ C., liquid crystal materials for low temperatures have also been desired.

As compounds having similar substituents on a terminal phenyl ring thereof to those of the compound of the present invention mentioned later, compounds expressed by the following formulas (1) or (2) are disclosed in Japanese patent application laid-open No.sho 61-501920/1986 (International patent application No. PCT/EP 85-00163, International publication No. WO 85/04874); and compounds expressed by the following formulas (3) or (4) are disclosed in U.S. Pat. No. 4,551,264:

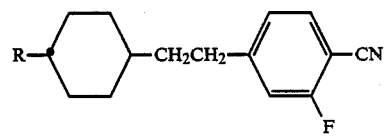

(1)

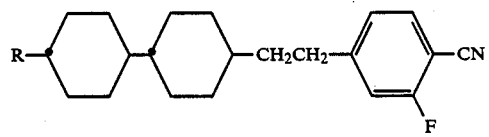

(2)

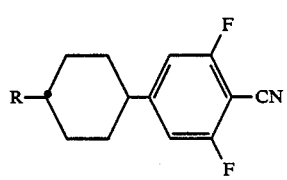

(3)

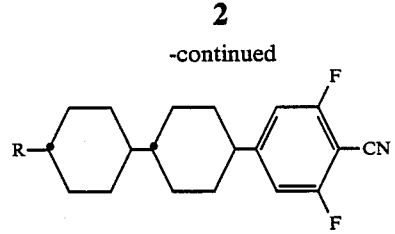

(4)

Further, a compound of the formula (I) wherein $l=1$ and $m=0$ is disclosed in Japanese patent application laid-open No. Sho 62-103057/1987, but this compound is somewhat inferior in the liquid crystal properties and moreover it has a high viscosity for a two-rings compound. Comparison of these compounds with the compound of the present invention will be shown in comparative test mentioned later.

SUMMARY OF THE INVENTION

An object of the present invention is to provide a compound having a relatively low viscosity, a broad nematic phase temperature range, a good compatibility with other liquid crystal components even at low temperatures and a positive large dielectric anisotropy value.

Another object of the present invention is to provide a liquid crystal composition having a low viscosity and capable of realizing a low driving threshold voltage of display elements.

The present invention resides in;

a cyclohexane derivative expressed by the formula

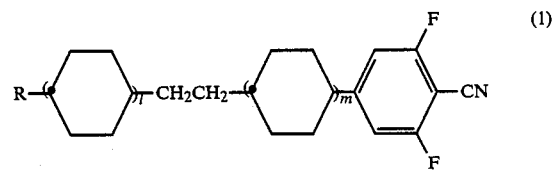

(1)

wherein R represents an alkyl group of 1 to 10 carbon atoms, l represents an integer of 1 or 2, m represents an integer of 0 or 1 and $l+m=2$, and a liquid crystal composition containing the compound.

DETAILED DESCRIPTION OF PREFERRED EMBODIMENTS

The cyclohexane compound expressed by the formula (I) includes compounds expressed by the following formula (a) or (b), which are preferred as a component of liquid crystal display materials:

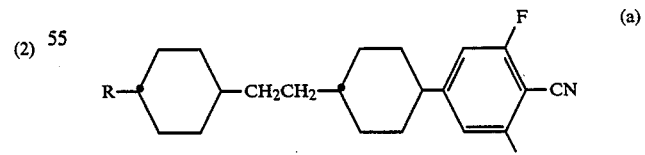

(a)

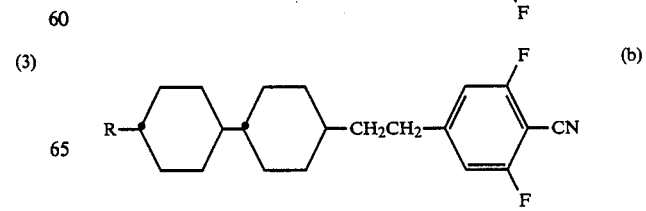

(b)

wherein R is as defined above.

The compounds expressed by the formula (a) or (b) have a large positive dielectric anisotropy value (abbreviated to Δε) and when they are used in admixture with a liquid crystal material having a relatively low viscosity, it is possible to lower the driving voltage of the resulting liquid crystal cell.

The compound of the present invention has a specific feature of a good compatibility with other existing liquid crystals at low temperatures, and further had specific features preferred as a liquid crystal component such as low viscosity, broad nematic phase temperature range, etc., in well-balanced manner.

Next, an example of preparation of the cyclohexane derivative of the present invention will be illustrated.

The above compound (b) can be prepared through the following route:

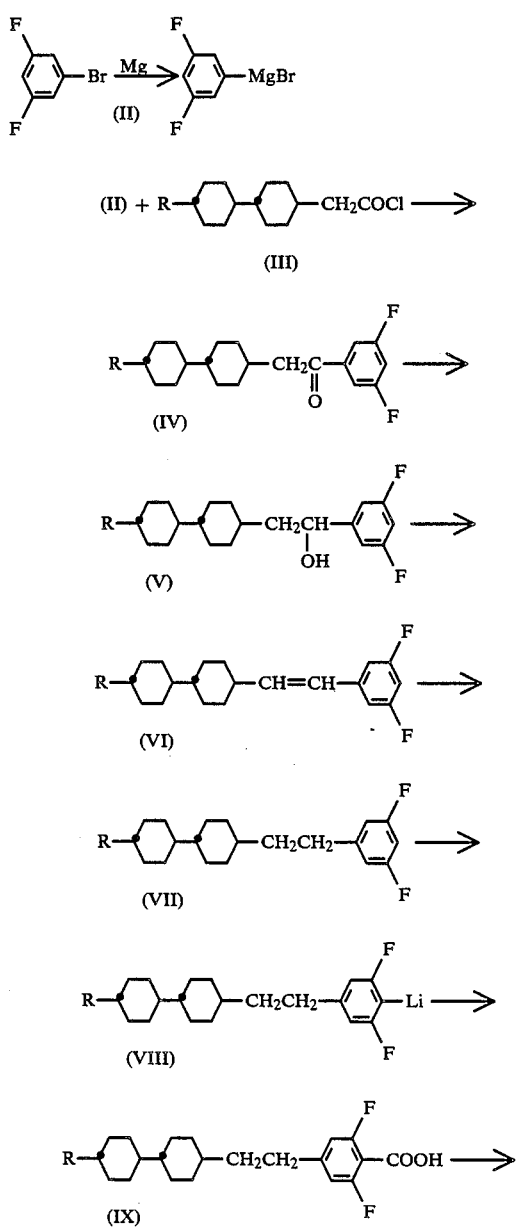

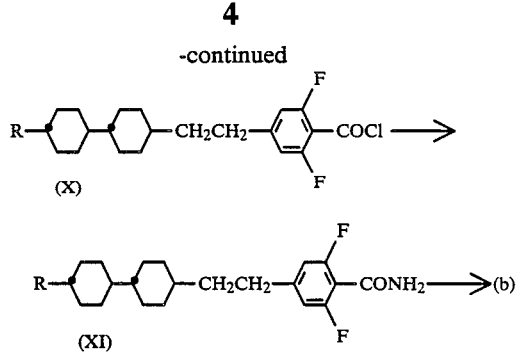

First, an acid chloride expressed by the formula (III) is reacted with a Grignard reagent (II) obtained from 3,5-difluorobromobenzene and metal magnesium in the presence of a suitable catalyst such as Ni(acac)$_2$, Fe(acec)$_3$, FeCl$_3$, Ni(PPh$_3$)$_2$Cl$_2$, etc. to obtain a ketone derivative of the formula (IV). This reaction is preferably carried out in a solvent such as diethyl ether, tetrahydrofuran, etc. at a temperature of about $-70°$ to $0°$ C. The ketone derivative of (IV) is then reduced with a suitable reducing agent such as lithium aluminum hydride, sodium borohydride, etc. to obtain an alcohol derivative of the formula (V), which is then subjected to dehydration reaction in the presence of a catalyst as mentioned later, in an inert organic solvent, at a reflux temperature under the atmosphere to obtain an ethylene derivative of the formula (VI). As the catalyst, a Lewis acid such as aluminium chloride, tin tetrachloride, titanium tetrachloride, etc., oxyacids such as sulfuric acid, phosphoric acid, toluenesulfonic acid, etc. and the like may be used. The compound of (VI) is successively subjected to catalytic reduction reaction, followed by subjecting the reaction material to a suitable purification treatment, whereby an ethane compound of the formula (VII) can be isolated. A suitable lithiating agent is then reacted with the compound of (VII) to obtain a lithium salt of a compound to the formula (VIII), which is reacted with carbon dioxide without isolating it to obtain a carboxylic acid of the formula (IX), which is chlorinated to obtain an acid chloride (X), which is converted into an acid amide (XI), which is subjected to dehydration reaction to obtain the objective cyclohexane compound of the formula (I).

Further, the above-mentioned compound (a) may be prepared through the following route:

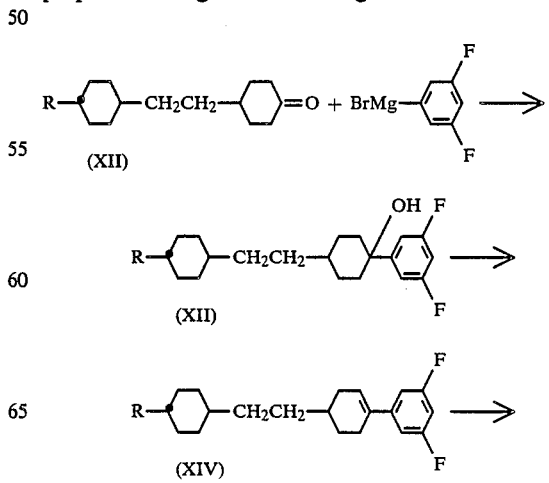

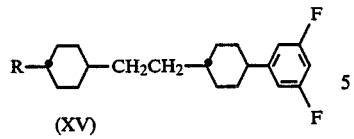

(XV)

Namely, a ketone expressed by the formula (XII) is reacted with a Grignard reagent (II) obtained from 3,5-difluorobromobenzene and metal magnesium to obtain an alcohol derivative of the formula (XIII), which is then subjected to dehydration reaction in the presence of a dehydrating catalyst as mentioned above in an inert organic solvent to obtain a cyclohexene derivative of the formula (XIV), which is then subjected to catalytic reduction, followed by subjecting the reaction material to a suitable purification treatment to obtain a compound of the formula (XV), which is subjected to the same procedure as the above-mentioned one wherein the compound of the formula (XI) is obtained from the compound of the formula (VII), to obtain the cyclohexane derivative of the formula (a).

The liquid crystal composition of the present invention contains the compound expressed by the formula (I) in a proportion of 0.1 to 99%, preferably 1 to 40%, more preferably 5 to 20%.

Examples of compounds used as a component of the liquid crystal composition of the present invention in admixture with the compound expressed by the formula (I) are as follows:

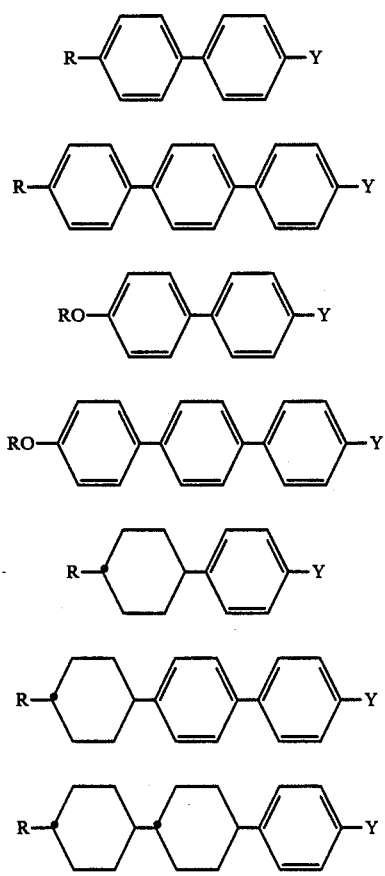

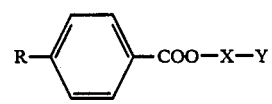

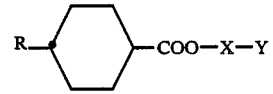

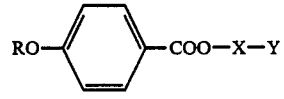

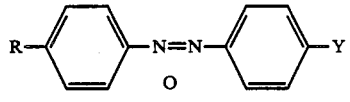

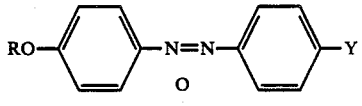

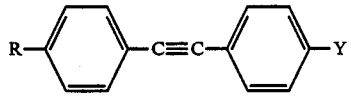

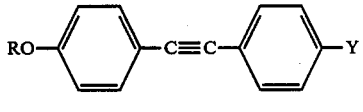

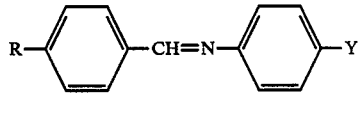

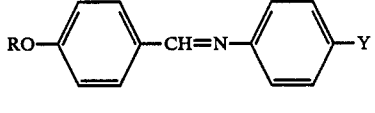

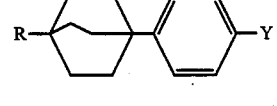

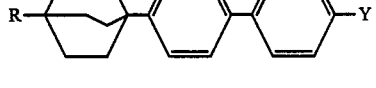

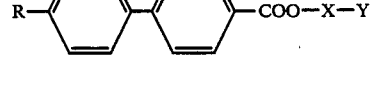

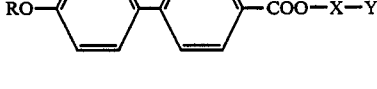

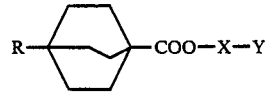

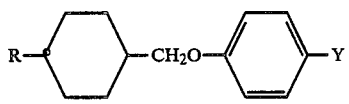

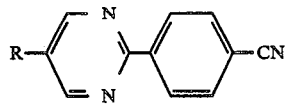

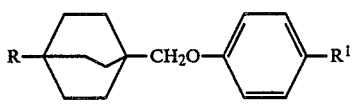

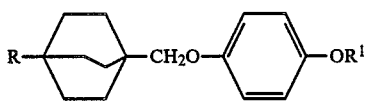

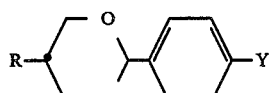

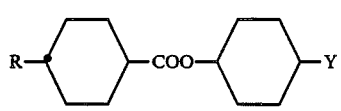

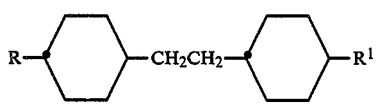

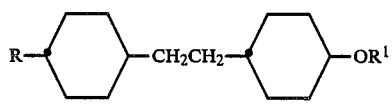

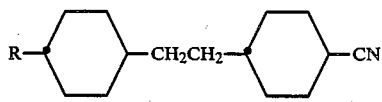

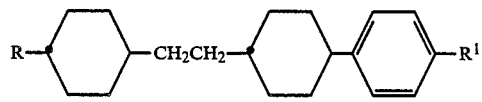

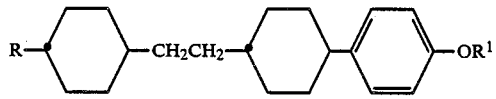

In the formulas (i) - (xxxiii), X represents

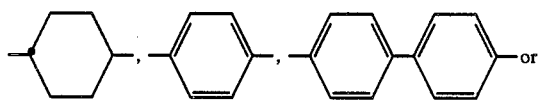

(xxii)

(xxiii)

(xxiv)

(xxv)

(xxvi)

(xxvii)

(xxviii)

(xxix)

(xxx)

(xxxi)

(xxxii)

(xxxiii)

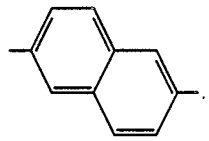

Y represents —CN or a halogen atom, $R^1$ or -$OR^1$ and R and $R^1$ each represent an alkyl group.

The present invention will be described in more detail by way of Examples, but it should not be construed to be limited thereto.

In the Examples, C-I point, C-N point and N-I point represent crystalline-isotropic liquid phase transition point, crystalline-nematic phase transition point and nematic-isotropic liquid phase transistion point, respectively.

EXAMPLE 1

4-[Trans-4-(trans-4-propylcyclohexyl)cyclohexylethyl]-2,6-difluorobenzonitrile (i) Trans-4-(trans-4-propylcyclohexyl)cyclohexylacetyl chloride (1.2 g, 0.25 mol) was dissolved in tetrahydrofuran (100 ml), followed by adding iron (III) acetylacetonate (4.4 g) to the solution, cooling the reactor down to −80° C., dropwise adding a tetrahydrofuran solution of a Grignard reagent prepared from 3,5-difluorobromobenzene (48.3 g, 0.25 mol) and magnesium (6.1 g, 0.25 mol) over one hour while keeping the reaction temperature at −80° to −70° C., thereafter returning the temperature to room temperature over 3 hours, adding the reaction material into dilute hydrochloric acid, extracting the resulting material with toluene (200 ml), washing the extract toluene solution with purified water, drying it over anhydrous sodium sulfate, filtering off the drying agent, distilling off toluene, collecting fractions containing the objective product by distillation under reduced pressure (b.p.:L 225° C./3 mmHg) and recrystallizing the fractions from ethyl alcohol to obtain colorless acicular 1-[trans-4-propylcyclohexyl)cyclohexylacetyl]-3,5-difluorobenzene (49.3 g, yield 54.5%, m.p.: 104.7° C.).

(ii) A solution of 1-[trans-4-(trans-4-propylcyclohexyl)-cyclohexylacetyl]-3,5-difluorobenzene (19.5 g) obtained in the above step (i), dissolved in tetrahydrofuran (50 ml) was added to a tetrahydrofuran suspension (50 ml) of lithium aluminium hydride (2.1 g, 0.054 mol) at 0° C., followed by agitating the mixture at 0° C. for 2 hours, adding 20% sulfuric acid (50 ml) to the reaction mixture to dissolve inorganic material, extracting the separated oily substance with heptane (100 ml), washing the extract solution with 10% sodium hydrogen carbonate aqueous solution and then with water till the washing water became neutral, drying the heptane solution over anhydrous sodium sulfate, distilling off heptane, adding p-toluene-sulfonic acid (0.3 g) and toluene (100 ml) to the remaining oily substance, heating the mixture under reflux to remove the resulting water to the outside of the reaction system, allowing the residue to cool down to room temperature after completion of the reaction, washing the toluene solution with water until the washing water became neutral, drying the toluene solution over anhydrous sodium sulfate, distilling off toluene and recrystallizing the residue from ethyl acetate to obtain β-[trans-4-(trans-4-propylcyclohexyl)cyclohexyl]-3,5-difluorostyrene (15.5 g). This product exhibited liquid crystal properties and its phase transition points were as follows:

C-N point: 66.5° C., N-I point: 132.3° C.

(iii) β-[trans-4-(trans-4-propylcyclohexyl)cyclohexyl]-3,5-difluorostyrene (15.5 g) obtained in the above step (ii) was dissolved in ethyl acetate (100 ml), adding 5% Pd/C catalyst (1.0 g), carrying out catalytic reduction reaction until hydrogen absorption at 20° C. ceased, removing the catalyst from the reaction mixture, distilling off ethyl acetate and recrystallizing the remaining oily substance from ethyl alcohol to obtain 1-[trans-4-(trans-4-propylcyclohexyl)cyclohexylethyl]-3,5-difluorobenzene (12.9 g). This product exhibited liquid crystal properties and its phase transition points were as follows:

C-N point: 50.8° C., N-I point: 92.2° C.

(iv) 1-[Trans-4-(trans-4-propylcyclohexyl)cyclohexylethyl]-3,5-difluorobenzene (12.9 g, 0.037 mol) obtained in the above step (iii) was dissolved in tetrahydrofuran (30 ml), followed by cooling the solution down to −80° C., adding a 15% hexane solution (20.5 cc) of butyllithium at −80° C. over 15 minutes, further agitating the mixture at this temperature for one hour, blowing $CO_2$ gas therein at −50° C., returning the temperature to room temperature in one hour, adding 6N hydrochloric acid (5 ml) to acidify the resulting material, extracting the freed carboxylic acid with heptane (50 ml), drying the heptane extract solution over anhydrous sodium sulfate, distilling off heptane from the extract solution and recrystallizing the remaining solids from acetic acid (15 ml) to obtain colorless acicular 4-[trans-4-(trans-4-propylcyclohexyl)-cyclohexylethyl]-2,6-difluorobenzoic acid (9.1 g, yield 63%). This product exhibited liquid crystal phases and its phase transition points were as follows:

C-N point: 231.1° C., N-I point: 252.4° C.

(v) An acid chloride prepared from 4-[trans-4-(trans-4-propylcyclohexyl)cyclohexylethyl]-2,6-difluorobenzoic acid obtained above in the step (iv) (6.3 g, 0.016 mol) and thionyl chloride was dissolved in dried 1,4-dioxane (20 ml), followed by adding the solution to a mixture of ice (50 g) with aqueous ammonia (30 ml), vigorously agitating the mixture and filtering off deposited bulk material to obtain the corresponding acid amide (4.2 g).

(vi) Toluene (50 ml) and thionyl chloride (50 ml) were added to the acid amide obtained above in the step (v), followed by reacting the mixture on heating under reflux for 10 hours, allowing the resulting material to cool down after the reaction, adding it into ice water (100 g), agitating the mixture, separating the toluene layer, washing it with 2N NaOH aqueous solution (50 cc), further washing with water until the washing water became neutral, drying it over anhydrous sodium sulfate, filtering off the drying agent, distilling off toluene from the toluene solution and recrystallizing the remaining oily substance from ethyl acetate (10 ml) to obtain the objective 4-[trans-4-propylcyclohexyl)cyclohexylethyl]-2,6-difluorobenzonitrile (3.1 g, yield 52%). This compound exhibited broad liquid crystal phases and the phase transition points were as follows:

C-N point: 95.6° C., N-I point: 137.8° C.

The following compounds are similarly prepared from the corresponding acid chlorides:

4-[trans-4-(trans-4-methylcyclohexyl)cyclohexylethyl]-2,6-difluorobenzonitrile,

4-[trans-4-(trans-4-ethylcyclohexyl)cyclohexylethyl]-2,6-difluorobenzonitrile,

4-[trans-4-(trans-4-butylcyclohexyl)cyclohexylethyl]-2,6-difluorobenzonitrile,

4-[trans-4-(trans-4-pentylcyclohexyl)cyclohexylethyl]-2,6-difluorobenzonitrile (C-N point: 69.5° C., N-I point: 142.4° C.), 4-[trans-4-(trans-4-hexylcyclohexyl)cyclohexylethyl]-2,6-difluorobenzonitrile, 4-[trans-4-(trans-4-heptylcyclohexyl)cyclohexylethyl]-2,6-difluorobenzonitrile, 4-[trans-4-(trans-4-octylcyclohexyl)cyclohexylethyl]-2,6-difluorobenzonitrile, 4-[trans-4-(trans-4-nonylcyclohexyl)cyclohexylethyl]-2,6-difluorobenzonitrile, 4-[trans-4-(trans-4-decylcyclohexyl)cyclohexylethyl]-2,6-difluorobenzonitrile.

EXAMPLE 2

Using as a raw material, [trans-4-(trans-4-ethylcyclohexylethyl)cyclohexyl]-3,5-difluorobenzene (which exhibited liquid crystal phases, C-I point being 44.8° C. and N-I point, 40.9° C.), prepared from 3,5-difluorobromobenzene and 4-[trans-4-ethylcyclohexylethyl)cyclohexanone, 4-[trans-4-(trans-4-ethylcyclohexylethyl)cyclohexyl]-2,6-difluorobenzonitrile was obtained in the same manner as in Example 1. This product exhibited broad liquid crystal phases, C-N point being 51.0° C. and N-I point being 107.2° C.

The following compounds are similarly obtained:

4-[trans-4-(trans-4-methylcyclohexylethyl)cyclohexyl]-2,6-difluorobenzonitrile,

4-[trans-4-(trans-4-propylcyclohexylethyl)cyclohexyl]-2,6-difluorobenzonitrile,

4-[trans-4-(trans-4-butylcyclohexylethyl)cyclohexyl]-2,6-difluorobenzonitrile,

4-[trans-4-(trans-4-pentylcyclohexylethyl)cyclohexyl]-2,6-difluorobenzonitrile,

4-[trans-4-(trans-4-hexylcyclohexylethyl)cyclohexyl]-2,6-difluorobenzonitrile,

4-[trans-4-(trans-4-heptylcyclohexylethyl)cyclohexyl]-2,6-difluorobenzonitrile,

4-[trnas-4-(trans-4-octylcyclohexylethyl)cyclohexyl]-2,6-difluorobenzonitrile,

4-[trans-4-(trans-4-nonylcyclohexylethyl)cyclohexyl]-2,6-difluorobenzonitrile,

4-[trans-4-(trans-4-decylcyclohexylethyl)cyclohexyl]-2,6-difluorobenzonitrile,

EXAMPLE 3

A liquid crystal composition A consisting of
4-(trans-4-propylcyclohexyl(benzonitrile, 30 wt.%
4-(trans-4-pentylcyclohexyl(benzonitrile, 40 wt.% and
4-(trans-4-heptylcyclohexyl(benzonitrile, 30 wt.%
has a N-I point of 52.1° C., a dielectric anisotroy value $\Delta\epsilon$ of 10.7 and a viscosity at 20° C. (hereinafter abbreviated to $\eta_{20}$) of 22.4 cp. This composition was sealed in a TN mode cell of 10 μm thick and its specific features at 20° C. were measured to exhibit a threshold voltage of 1.57 V and a saturation voltage of 2.13 V. When 4-[trans-4-(trans-4-ethylcyclohexylethyl)cyclohexyl]-2,6-difluorobenzonitrile (15 parts by weight) as a compound of the present invention in Example 2 was added to the liquid crystal composition A (85 parts by weight), the N-I point of the resulting liquid crystal mixture rose up to 56.7° C. and its $\Delta\epsilon$ was 12.9. Its viscosity at 20° C. rose somewhat up to 26.4 cp. When this liquid crystal mixture was sealed in the above-mentioned TN mode cell, the threshold voltage and the saturation voltage of the resulting cell decreased down to 1.36 V and 2.40 V, respectively.

EXAMPLE 4

When 4-[trans-4-(trnas-4-propylcyclohexyl)cyclohexylethyl]-2,6-difluorobenzonitrile (15 parts by weight) as a compound of the present invention shown in Example 1 was added to the liquid crystal composition A (85 parts by weight), the resulting liquid crystal mixture exhibited a N-I point of 62.2, a $\Delta\epsilon$ of 12.6 and a viscosity at 20° C. of 26.5 cp. When this liquid crystal mixture was sealed in the above-mentioned TN mode cell, the resulting threshold voltage and saturation voltage were 1.38 V and 2.38 V.

Comparative example 1

4-(Trans-4-propylcyclohexylethyl)-2,6-difluorobenzonitrile was prepared in the same manner as in Example 1. This product has a m.p. of 27.3 ° C. and no liquid crystal phase was observed.

A liquid crystal compositino B consisting of
4-(trans-4-propylcyclohexyl)benzonitrile, 24 wt.%
4-(trans-4-pentylcyclohexyl)benzonitrile, 36 wt.%
4-(trans-4-heptylcyclohexyl)benzonitrile, 25 wt.% and
4-[4-(trans-4-pentylcyclohexyl)phenyl]benzonitrile, 15 wt.%
has a N-I point of 72.0° C., a $\Delta\epsilon$ value of 11.6 and a viscosity at 20° C. of 27.8 cp. This composition B was filled in a TN mode cell of 10 $\mu$m thick and its specific features at 20° C. were measured to give a threshold voltage of 1.75 V and a saturation voltage of 2.40 V. When the above-mentioned 4-(trans-4-propylcyclohexylethyl)-2,6-difluorobenzonitrile (15 parts by weight) was added to the composition B, the resulting liquid crystal mixture exhibited a N-I point of 56.0° C., a $\Delta\epsilon$ of 13.4 and a viscosity at 20° C. of 29.2 cp. When this liquid crystal mixture was filled in the above TN mode cell, the threshold voltage and the saturation voltage at 20° C. were 1.26 V and 2.15 V, respectively.

Comparative test

Comparisons of the compounds of the above-mentioned formulas (1)–(4) and the two-rings cyclohexane compound shown in Comparative example 1, with the compound of hte present invention in the aspect of low temperature compatibility were carried out as follows:

Liquid crystal composition A shown in Example 3 or liquid crystal composition B shown in Comparative example 1 (each 85 parts by weight) was added to the respective compounds of the formulas (1)–(4) wherein R each represents n-$C_3H_7$ (each 15 parts by weight) to prepare 4 kinds of liquid crystal mixtures. These 4 kinds of liquid crystal mixtures, liquid crystal mixtures prepared in Examples 3 and 4 and Comparative example 1 and liquid crystal compositions A and B, that is, 9 kinds of liquid crystal mixtures in total, were respectively stored in a refrigerator at 31 40° C. for 30 days to observe the presence or absence of crystal deposition. The results are shown in Table 1. In the column of low temperature compatibility in Table 1, the symbol o indicates no crystal deposition and the symbol × indicates crystal deposition during the storage. Further, the respective extrapolated values of $\Delta\epsilon$ and $\eta_{20}$ of compounds mixed with the respective liquid crystal mixtures in 15% by weight are shown in Table 1 together with those of compositions A and B.

TABLE 1

| Compound mixed with composiiton in 15 wt. % | L.C. mixture mixed with compd. in 85 wt. % | $\Delta\epsilon$ | $\eta$ 20(c.p.) | Low temp compatibility |
|---|---|---|---|---|
| 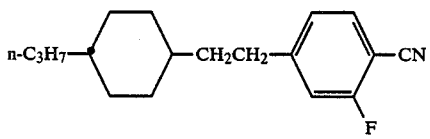 (1) | Composition B | 18.9 | 31.0 | |
| 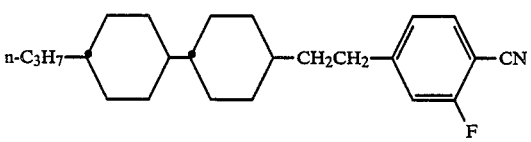 (2) | Composition A | 17.2 | 46.1 | |
| 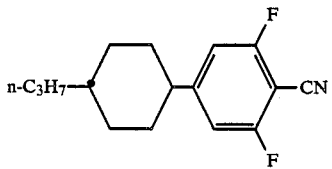 (3) | Composition B | 23.7 | 48.9 | x |

TABLE 1-continued

| Liquid crystal mixture | | | | |
|---|---|---|---|---|
| Compound mixed with composiiton in 15 wt. % | L.C. mixture mixed with compd. in 85 wt. % | Δε | η 20(c.p.) | Low temp compatibility |
| n-C₃H₇—◯—◯—⌬(F)(F)—CN | (4) Composition A | 23.4 | 64.7 | x |
| n-C₃H₇—◯—CH₂CH₂—⌬(F)(F)—CN | Composition B | 23.6 | 37.1 | |
| C₂H₅—◯—CH₂CH₂—◯—⌬(F)(F)—CN | Composition A | 25.4 | 49.0 | |
| n-C₃H₇—◯—◯—CH₂CH₂—⌬(F)(F)—CN | Composition A | 23.4 | 49.7 | |
| Liquid crystal composition A | | 10.7 | 22.4 | x |
| Liquid crystal composition B | | 11.6 | 27.8 | x |

What we claim is:

1. A cyclohexane derivative expressed by the formula

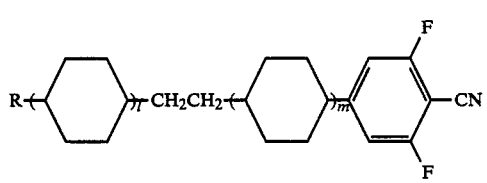

wherein R represents an alkyl group of 1 to 10 carbon atoms, l represents an integer 1 or 2, m represents an integer of 0 or 1 and l+m=2.

2. A cyclohexane derivative according to claim 1, which is expressed by the formula

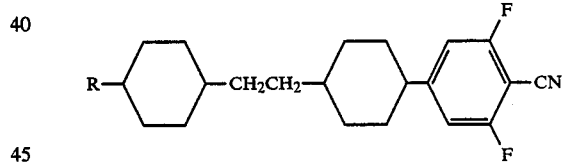

wherein R represents an alkyl group of 1 to 10 carbon atoms.

3. A cyclohexane derivative according to claim 1, which is expressed by the formula

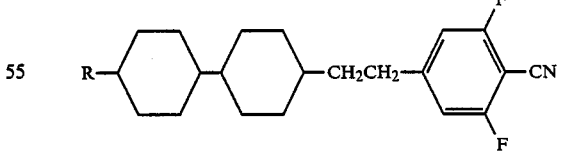

wherein R represents an alkyl group of 1 to 10 carbon atoms.

4. A liquid crystal composition comprising at least two components at least one of which is a cyclohexane derivative as set forth in claim 1.

* * * * *